(12) United States Patent
Langley et al.

(10) Patent No.: US 7,857,744 B2
(45) Date of Patent: Dec. 28, 2010

(54) BLOOD PROCESSING APPARATUS WITH FLARED CELL CAPTURE CHAMBER AND METHOD

(75) Inventors: Robert W. Langley, Westminster, CO (US); Linda A. Taylor, Littleton, CO (US); Timothy Michael Taga, Broomfield, CO (US)

(73) Assignee: CaridianBCT, Inc., Lakewood, CO (US)

( * ) Notice: Subject to any disclaimer, the term of this patent is extended or adjusted under 35 U.S.C. 154(b) by 755 days.

(21) Appl. No.: 11/765,091

(22) Filed: Jun. 19, 2007

(65) Prior Publication Data

US 2008/0318756 A1  Dec. 25, 2008

(51) Int. Cl.
*B04B 7/08* (2006.01)
(52) U.S. Cl. ........................................ 494/45
(58) Field of Classification Search ............... 494/17, 494/18, 42, 60, 45; 220/669
See application file for complete search history.

(56) References Cited

U.S. PATENT DOCUMENTS

| | | | |
|---|---|---|---|
| 2,616,619 A | 11/1952 | MacLeod | |
| 3,391,597 A | 7/1968 | Gropper | |
| 4,187,979 A * | 2/1980 | Cullis et al. | 494/42 |
| 5,674,173 A | 10/1997 | Hlavinka et al. | |
| 5,722,926 A | 3/1998 | Hlavinka et al. | |
| 5,906,570 A | 5/1999 | Langley et al. | |
| 5,939,319 A | 8/1999 | Hlavinka et al. | |
| 5,951,877 A | 9/1999 | Langley et al. | |
| 6,051,146 A | 4/2000 | Green et al. | |
| 6,053,856 A | 4/2000 | Hlavinka | |
| 6,334,842 B1 | 1/2002 | Hlavinka et al. | |
| 6,354,986 B1 | 3/2002 | Hlavinka et al. | |

(Continued)

FOREIGN PATENT DOCUMENTS

DE    2658926    6/1978

(Continued)

OTHER PUBLICATIONS

Figdor et al, "Theory and Practice of Centrifugal Elutriation (CE), Factors Influencing the Separation of Human Blood Cells", *Cell Biophysics 5*, 105-118, 1983.

(Continued)

*Primary Examiner*—Walter D Griffin
*Assistant Examiner*—Timothy Cleveland
(74) *Attorney, Agent, or Firm*—John R. Merkling; Edna M. O'Connor; Laura B. Arciniegas (57) ABSTRACT

A cell separation set for separating blood components, having a cell separation chamber with a first entry section having a wall with an outwardly flared curve, the entry section having an axial length and an inmost maximum diameter perpendicular to the axial length, the axial length being greater than the inmost maximum diameter. The cell separation chamber further comprises a separation section having a wall comprising an inward curve. A transition section between the entry section and the separation section has a wall comprising a second inward curve, the second inward curve being different from said first inward curve. The first curve may be tangent to the second curve at a first junction between the first and second curves and the second curve may be tangent to the third curve at a second junction between the second and third curves.

20 Claims, 7 Drawing Sheets

U.S. PATENT DOCUMENTS

| | | |
|---|---|---|
| 6,616,019 B2 * | 9/2003 | D'Alessio et al. ........... 222/566 |
| 7,201,848 B2 | 4/2007 | Antwiler et al. |
| 2003/0116512 A1 | 6/2003 | Antwiler et al. |
| 2005/0051466 A1 | 3/2005 | Carter et al. |

FOREIGN PATENT DOCUMENTS

| | | |
|---|---|---|
| DE | 2701976 | 7/1978 |
| DE | 3700122 | 7/1988 |
| DE | 3734170 | 7/1989 |
| EP | 0406485 | 1/1991 |
| EP | 0408462 | 1/1991 |
| WO | WO96/33203 | 10/1996 |

OTHER PUBLICATIONS

Grabske, Robert, "Separating Cell Populations by Elutriation", Beckman Instruments, 1978, p. 1-8.

Lutz et al, "Large-Scale Cell Separation by Centrifugal Elutriation", *Analytical Biochemistry*, 1992, 200:376-380.

Sanderson, et al, "Design Principles for a Counterflow Centrifugation Cell Separation Chamber", *Analytical Biochemistry*, 1976, 71:615-622.

Tulp et al, "A Separation Chamber to Sort Cells and Cell Organelles by Weak Physical Forces . . . ", *J. of Immunological Methods*, 1984, 69:281-295.

International Search and Written Opinion, PCT/US2008/060631, mailed Oct. 13, 2008.

\* cited by examiner

BLOOD PROCESSING APPARATUS WITH FLARED CELL CAPTURE CHAMBER AND METHOD

BACKGROUND OF THE INVENTION

1. Field of the Invention

The present invention relates to an apparatus and method for separating particles or components of a fluid. The invention has particular advantages in connection with separating blood components, such as white blood cells and platelets.

The flared elutriation chamber described herein may be used with various blood-separation apparatus, such as the apparatus described in U.S. Pat. No. 5,722,926, issued Mar. 3, 1998; U.S. Pat. No. 5,951,877, issued Sep. 14, 1999; U.S. Pat. No. 6,053,856, issued Apr. 25, 2000; U.S. Pat. No. 6,334,842, issued Jan. 1, 2002; U.S. patent application Ser. No. 10/884,877 filed Jul. 1, 2004; U.S. Pat. No. 7,201,848. The entire disclosure of each of these U.S. patents and patent applications is incorporated herein by reference.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of devices and processes where particles are either separated from one another or from liquid.

In the medical field, it is often necessary to filter blood. Whole blood consists of various liquid components and particle components. The liquid portion of blood is largely made up of plasma, and the particle components include red blood cells (erythrocytes), white blood cells (leukocytes), and platelets (thrombocytes). While these constituents have similar densities, their average density relationship, in order of decreasing density, is as follows: red blood cells, white blood cells, platelets, and plasma. In addition, the particle components are related according to size, in order of decreasing size, as follows: white blood cells, red blood cells, and platelets. Most current purification devices rely on density and size differences or surface chemistry characteristics to separate and/or filter the blood components.

Typically, donated platelets are separated or harvested from other blood components using a centrifuge. White cells or other selected components may also be harvested. The centrifuge rotates a blood separation vessel to separate components within the vessel or reservoir using centrifugal force. In use, blood enters the separation vessel while it is rotating at a very rapid speed and centrifugal force stratifies the blood components, so that particular components may be separately removed. Components are removed through ports arranged within stratified layers of blood components.

White blood cells and platelets in plasma form a medium density stratified layer or "buffy coat". Because typical centrifuge collection processes are unable to consistently and satisfactorily separate white blood cells from platelets in the buffy coat, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5-20% of the platelets. These conventional filters may also reduce "platelet viability" meaning that once passed through a filter a percentage of the platelets cease to function properly and may be partially or fully activated. In addition, porous filters may cause the release of bradykinin, an inflammation mediator and vasodialator, which may lead to hypotensive episodes in a patient. Porous filters are also expensive and often require additional time-consuming manual labor to perform a filtration process. Although porous filters are effective in removing a substantial number of white blood cells, activated platelets may clog the filter. Therefore, the use of at least some porous filters is not feasible in on-line processes.

Another separation process is one known as centrifugal elutriation. This process separates cells suspended in a liquid medium without the use of a membrane filter. In one common form of elutriation, a cell batch is introduced into a flow of liquid elutriation buffer. This liquid, which carries the cell batch in suspension, is then introduced into a funnel-shaped chamber located on a spinning centrifuge. As additional liquid buffer solution flows through the chamber, the liquid sweeps smaller, less dense, slower-sedimenting cells toward an elutriation boundary within the chamber, while larger, more dense, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively faster-sedimenting cells may be removed from the chamber. Depending on conditions such as flow rate or viscosity, for example, sedimentation rate will be dominated by either the size or density of the cells.

Thus, centrifugal processing separates particles having different sedimentation velocities. Stoke's law describes sedimentation velocity ($V_S$) of a spherical particle as follows:

$$V_S = ((D^2_{cell} * (\rho_{cell} - \rho_{medium}))/(18 * \mu_{medium})) * \omega^2 r$$

where D is the diameter of the cell or particle, $\rho_{cell}$ is the density of the particle, $\rho_{medium}$ is the density of the liquid medium, $\mu_{medium}$ is the viscosity of the medium, and $\omega$ is the angular velocity and r is the distance from the center of rotation to the cell or particle. Because the diameter of a particle is raised to the second power in Stoke's equation and the density of the particle is not, it is typically the size of a cell, rather than its density, that usually influences its sedimentation rate. This explains why larger particles generally remain in a chamber during centrifugal processing, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate, discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

For these and other reasons, there is a need to improve particle separation and/or separation of components of a fluid.

SUMMARY OF THE INVENTION

The present invention comprises a centrifuge for separating particles suspended in a fluid, particularly blood and blood components, and methods for controlling the centrifuge. The apparatus has a cell separation chamber mounted on a rotor, the cell separation chamber having a fluid inlet and a fluid outlet, the fluid inlet being radially outward from the fluid outlet, a first entry section adjacent the fluid inlet and radially inward from said inlet, the entry section having a wall comprising an outwardly flared curve forming a first surface, preferably a surface of rotation, about said axis of symmetry, the entry section having an axial length and an inmost maximum diameter perpendicular to the axial length, the axial length being greater than the inmost maximum diameter. The cell separation chamber may be part of a disposable blood processing vessel, which may be mounted on the rotor.

The outwardly flared curve of the cell entry chamber is generally defined by $$A=(A_0)\exp(CeXe)$$

where

A is the flow area (cross sectional area) at Xe, $A_0$ is the flow area perpendicular to the axis of symmetry at the inlet, Xe is the distance along the axis of symmetry from the inlet, 0<Xe<Le, Le is the length of the entry section, and Ce is a design constant.

The cell separation chamber further comprises a separation section spaced downstream from the entry section, the separation section having a wall comprising a first inward curve forming a second surface, preferably a surface of rotation, about said axis of symmetry. The first inward curve is generally defined by $$A=Asmax-(Asmax-Am)\exp(-CsXs)$$

where

A is the flow area perpendicular to the axis of symmetry at Xs.

Another feature of the invention is a transition or main section between the entry section and the separation section, the transition section having a wall comprising a second inward curve forming a third surface, preferably a surface of rotation, about said axis of symmetry, said second inward curve being different from said first inward curve. The first curve may be tangent to the second curve at a first junction between the first and second curves and the second curve may be tangent to the third curve at a second junction between the second and third curves.

The cell separation chamber may also have an exit section downstream from the separation section, said exit section comprising a frustro-conical wall tapering from the second wall of said separation section towards the axis of symmetry.

It is to be understood that both the foregoing general description and the following detailed description are exemplary, and are intended to provide further explanation of the invention as claimed.

DETAILED DESCRIPTION

To describe the present invention, reference will now be made to the accompanying drawings.

The preferred embodiment of the present invention includes an Elutra® blood component centrifuge manufactured by Gambro BCT, Inc. of Lakewood, Colo. The Elutra® centrifuge incorporates a one-omega/two-omega sealless tubing connection as disclosed in U.S. Pat. No. 4,425,112 to Ito, the entire disclosure of which is incorporated herein by reference. Although the embodiments of the invention are described in combination with the Elutra® centrifuge, this reference is made for exemplary purposes only and is not intended to limit the invention in any sense. Other centrifuges could be used, including, but not limited to, the COBE® Spectra apheresis system, in addition to the Trima®, Trima Accel®, Atreus®, and Spectra Optia™ systems, also manufactured by Gambro BCT Inc., as well as other elutriation devices used to separate blood components. The present invention may be advantageously used in a variety of centrifuge devices including, but not limited to, those commonly used to separate blood into its components. In particular, the present invention may be used with any centrifugal apparatus regardless of whether or not the apparatus employs a one-omega/two-omega seal-less tubing connection.

It will also be apparent that the teachings of the present invention can also be used for separating particles and blood cells as well as other cells. The description refers to both particles and cells and it is understood that both are used interchangeably without departing from the spirit of the invention. The teachings of the present invention further can be used with any elutriation system for separating particles and blood cells as well as other cells.

Figure 1:
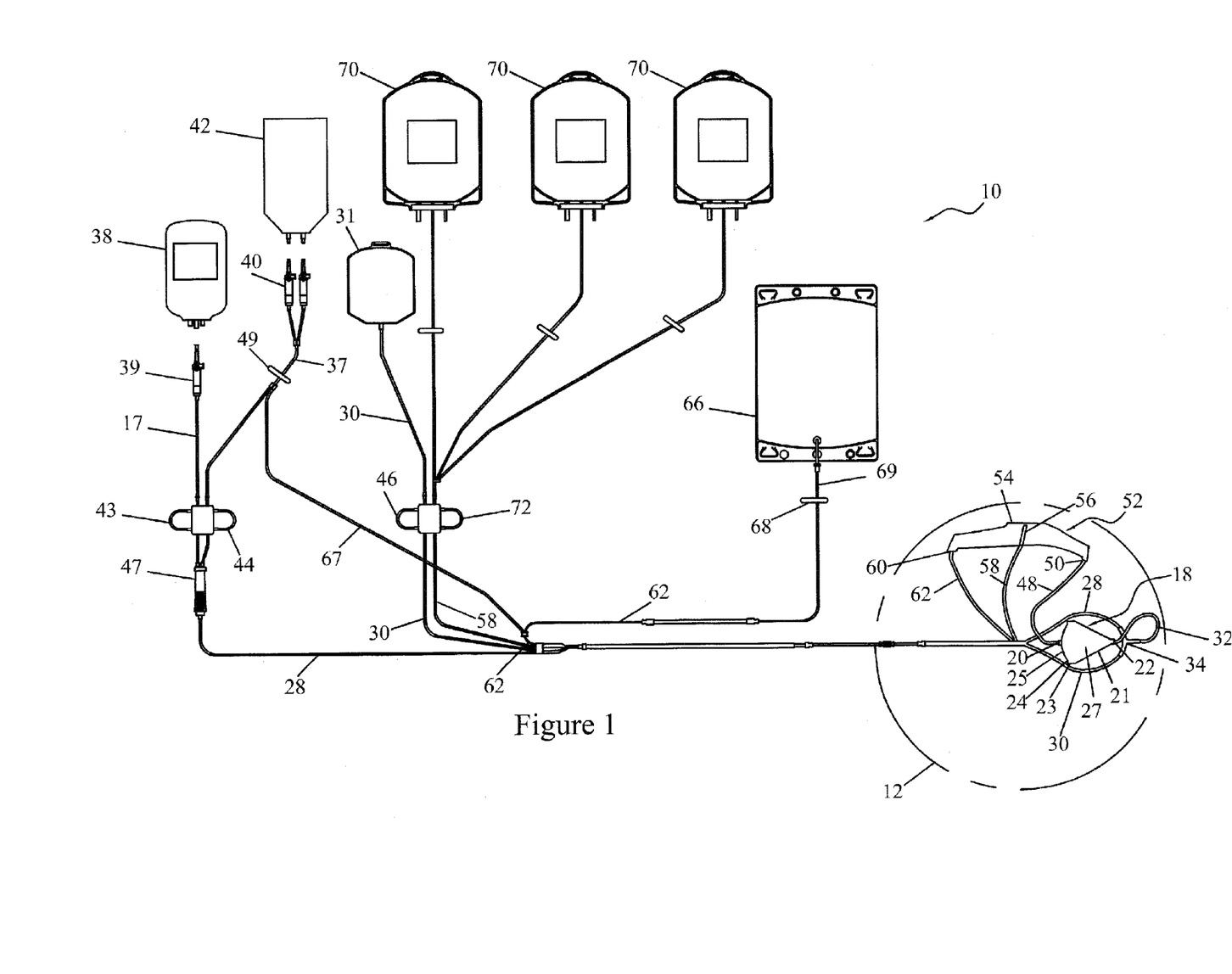
FIG. 1 is a schematic diagram of a particle separation system with a fluid separation chamber in accordance with an embodiment of the invention.

As illustrated in FIG. 1, the present invention may include a particle separation disposable system 10 for use with a centrifuge rotor 12. Preferably, the centrifuge rotor 12 is coupled to a motor (not shown) via an arm 14, shown in FIG. 2, so that the centrifuge rotor 12 rotates about its axis of rotation A—A.

Figure 2:
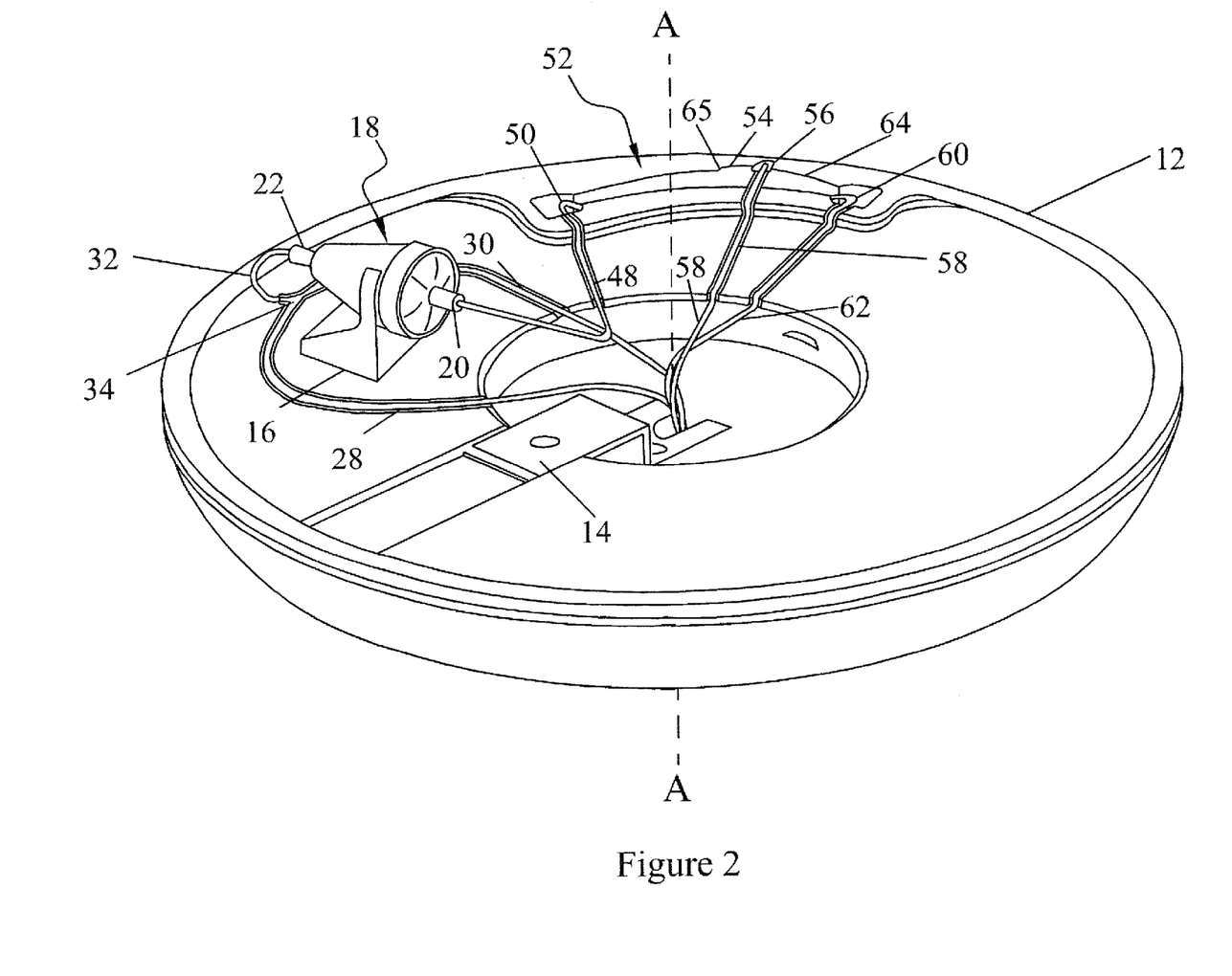
FIG. 2 is a perspective view of a fluid chamber and separation vessel mounted on a centrifuge rotor as depicted in FIG. 1.
Figure 3:
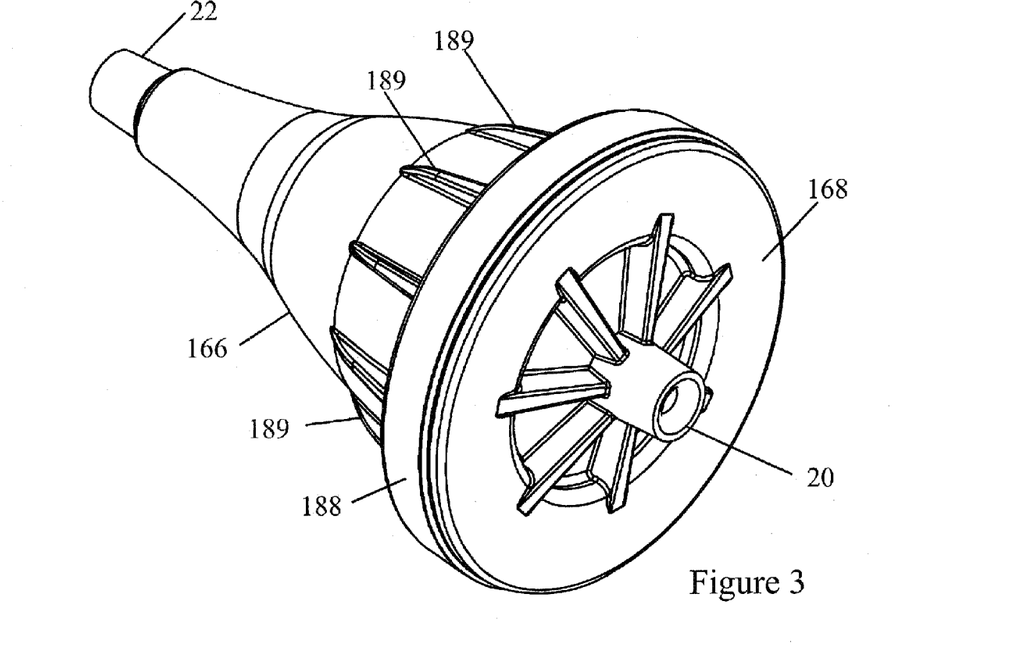
FIG. 3 is a perspective view of the fluid chamber of FIG. 1.
Figure 4:
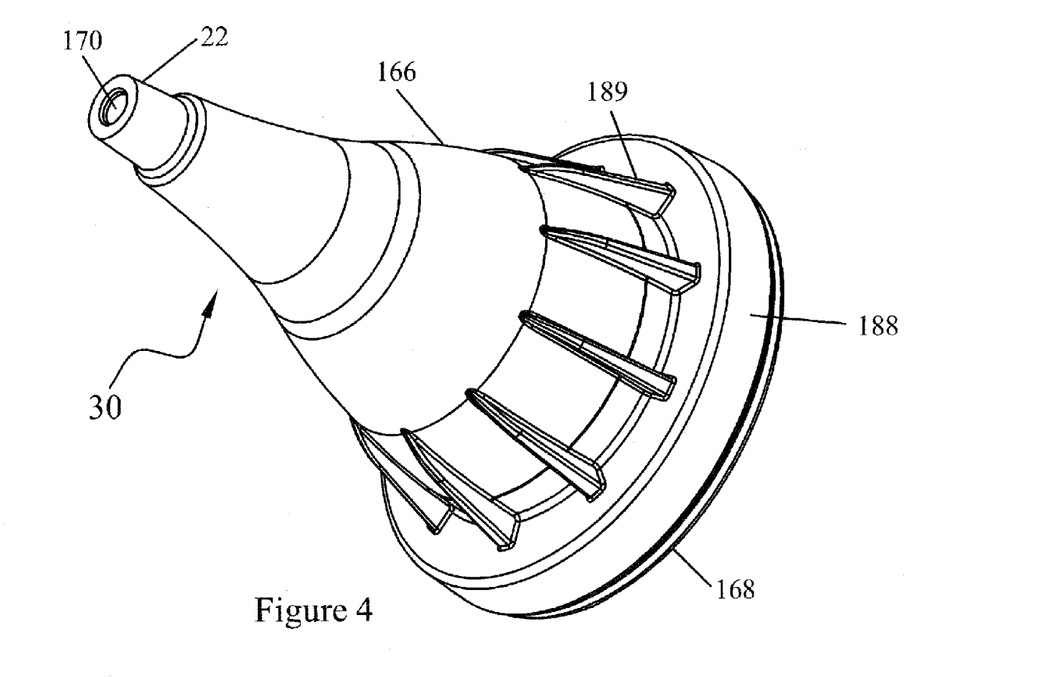
FIG. 4 is a rear perspective view of the fluid chamber of FIG. 3.
Figure 5:
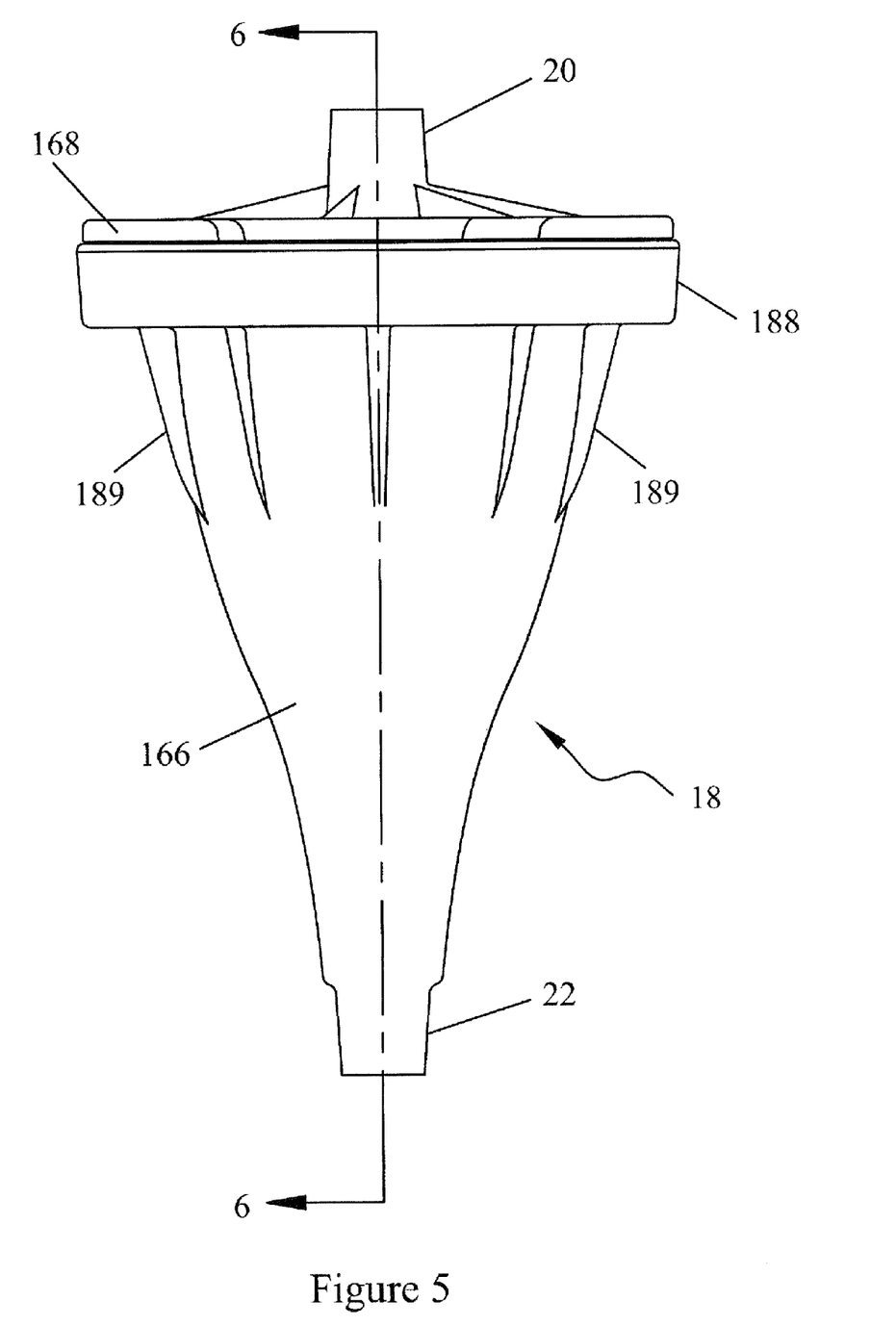
FIG. 5 is a plan view of the fluid chamber of FIG. 3.

As shown in FIG. 2, a holder 16 is provided on a top surface of the rotor 12. The holder 16 releasably holds a flared fluid chamber 18 on the rotor 12 such that an outlet 20 for components, hereinafter called the outlet of the fluid chamber 18, is positioned closer to the axis of rotation A—A than the inlet 22 of the fluid chamber 18. The holder 16 preferably orients the fluid chamber 18 on the rotor 12 with a longitudinal axis of the fluid chamber 18 in a plane transverse to the rotor's axis of rotation A—A. In addition, the holder 16 is preferably arranged to hold the fluid chamber 18 on the rotor 12 with the fluid chamber outlet 20 for components facing the axis of rotation A—A. Although the holder 16 retains the fluid chamber 18 on a top surface of the rotor 12, the fluid chamber 18 may also be secured to the rotor 12 at alternate locations, such as beneath the top surface of the rotor 12. It is also understood that the fluid chamber 18 could be secured by other well known fixative devices or by other methods other than the holder as shown. As shown in FIGS. 1, and 2, the inlet 22 and outlet 20 of the fluid chamber 18 are arranged along a longitudinal axis of the fluid chamber 18. A wall 21 of the fluid chamber 18 extends between the inlet 22 and outlet 20 thereby defining inlet 22, the outlet 20, the side and an interior of the fluid chamber 18.

Figure 6:
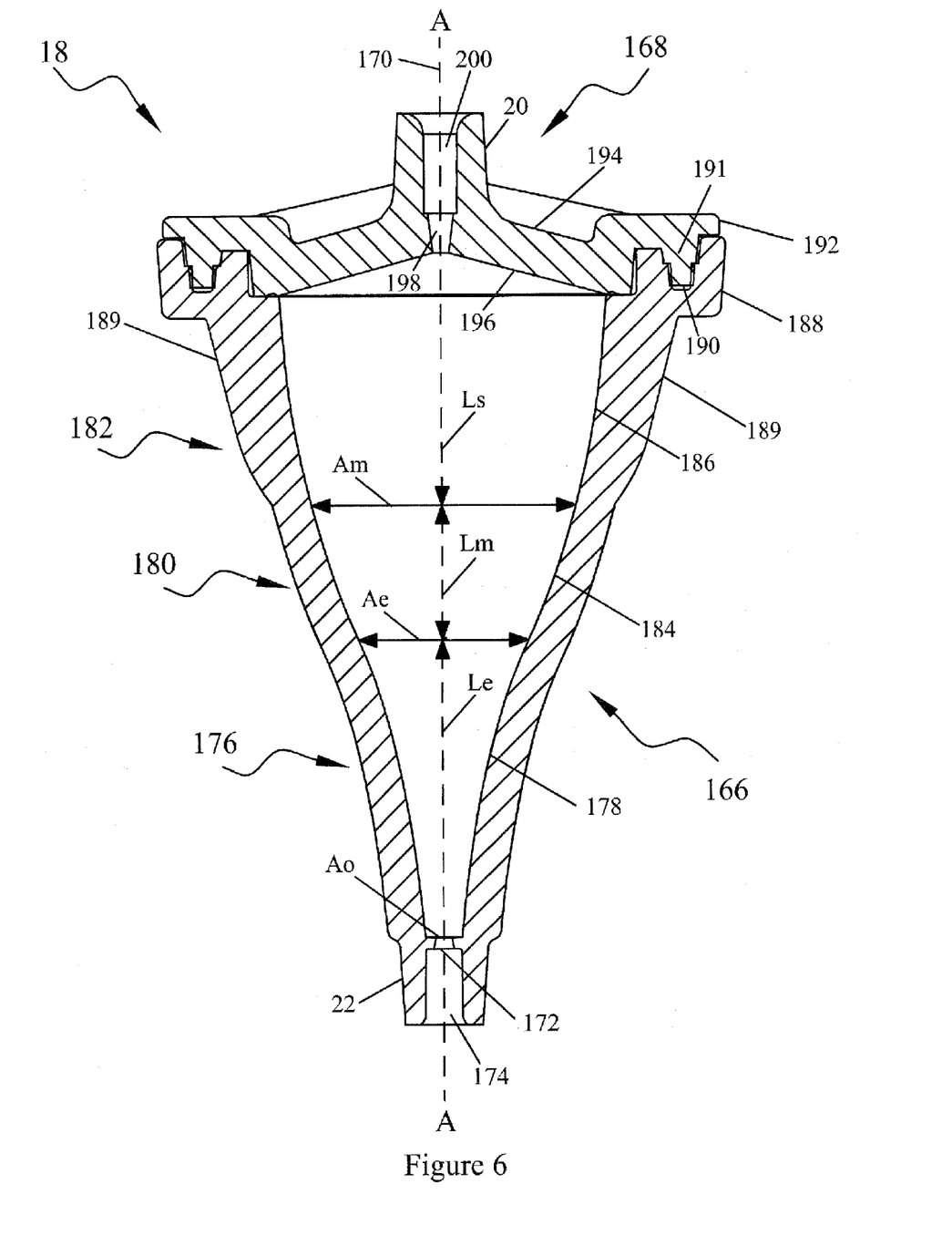
FIG. 6 is a cross sectional view of the fluid chamber of FIG. 5, taken along line 6-6.

As shown in FIG. 1 and FIG. 6, the fluid chamber 18 (further described below) includes two generally frusto-conical shaped sections 25, 27 joined together at a maximum cross-sectional area 23 of the fluid chamber 18. The interior of the fluid chamber 18 tapers (decreases in cross-section) from the maximum cross-sectional area 23 in opposite directions toward the inlet 22 and the outlet 20. Further important aspects of the flared fluid chamber 18 are set forth hereafter.

The fluid chamber 18 may be constructed from a unitary piece of plastic or from separate pieces joined together using known fixative or sealing methods to form separate sections of the fluid chamber 18. The fluid chamber 18 may be formed of a transparent or translucent co-polyester plastic, such as PETG, to allow viewing of the contents within the chamber interior with the aid of an optional strobe (not shown) during a separation procedure.

As shown in FIG. 1, the system 10, which depicts a disposable, includes a first conduit or line 28, second conduit or line 30, an inlet conduit or line 32 in fluid communication with the inlet 22 of the fluid chamber 18, and a three-way or Y connector 34 having three legs for flow or fluidly connecting the first line 28, second line 30, and inlet line 32. The first line 28 includes peristaltic pump loop 43 for flow-connecting the first line 28 with line 17, coupling 39 and a first source 38 containing fluid carrying particles to be separated from one another or the source blood product containing white blood cells. Likewise, the first line 28 is connected through pump loop 44 to conduit or line 37 which includes couplings 40 for flow-connecting the first line 28 with a second source 42 containing a low density diluting, sedimentation or elutriation fluid. The couplings 39 and 40 are preferably any type of common medical coupling devices, such as spikes or sterile tubing connectors. It is understood that lines or conduits 17 and 37 may be connected through a coupling (not shown) upstream of the inlet peristaltic pump loop so that a single loop pump (not shown) can be used.

The first line 28 includes pump loops 43 and 44. During use, the pump loops 43 and 44 are mounted in a peristaltic pump (not shown) for pumping the fluid or cell or particle product from the first source 38 and for pumping the diluting, sedimentation or elutriation fluid from the second source 42. The fluid and particles from the first source 38 and the diluting, sedimentation or elutriation fluid from the second source 42 flow through the first line 28 to the three-way connector 34. These substances then flow through the inlet line 32 into the inlet 22 of the fluid chamber 18. In the fluid chamber 18, which turns with rotor 12 when mounted thereon, the particles in the centrifugal field separate according to differences in sedimentation velocity leaving faster sedimenting particles in the fluid chamber 18 and allowing some slower sedimenting particles to flow from the fluid chamber 18 as will be described below.

As the fluid chamber 18 is loaded with particles, the fluid and particles having a relatively slower sedimentation velocity, which generally includes plasma, platelets, and possibly some white blood cells, flow through the fluid chamber outlet 20 into conduit or line 48. As shown in FIGS. 1 and 2, the line 48 is connected to an inlet 50 of separation vessel 52 or particle concentrator mounted on the centrifuge rotor 12. As described below, the separation vessel 52 concentrates particles from fluid. Also, during any elutriation process to separate the white blood cells into subsets, such separated subsets will flow from the fluid chamber 18 to the separation vessel 52.

Adjacent to an outer portion of the centrifuge rotor 12, the separation vessel 52 has a collection well 54 for collecting particles flowing into the separation vessel 52. Rotation of centrifuge rotor 12 sediments particles into the collection well 54 while slower sedimenting fluid and possibly some slower sedimenting particles remain above a top boundary of the collection well 54. The collected particles in the collection well 54 can include any cells or particles that have exited the fluid chamber 18, including a separated subset of white blood cells, as noted above.

The collection well 54 has a particle concentrate outlet 56 connected to a particle concentrate line or conduit 58. The particle concentrate line 58 removes particles retained in the collection well 54 along with a small portion of fluid. The separation vessel 52 also includes a fluid outlet 60 connected to a fluid outlet line or conduit 62. The fluid outlet line 62 removes fluid flowing above a top boundary of the collection well 54. This fluid may include plasma or elutriation buffer or low density fluid. In addition, the fluid outlet line 62 may remove some slower sedimenting particles flowing above the top boundary layer past the collection well 54.

Fluid outlet 60 is located at or adjacent to one end of the separation vessel 52, and the inlet 50 is located at or adjacent to an opposite end of the separation vessel 52. This spacing ensures ample time for separation of particles from fluid, collection of a substantial number of particles in the collection well 54, and corresponding removal of a substantial number of particles including any separated subsets of white blood cells through the particle concentrate line 58.

In the embodiment shown in FIG. 2, the separation vessel 52 is placed in a groove 64 formed in the rotor 12. Preferably, the separation vessel 52 is a channel formed of a semi-rigid material so that a valley 65 in an outer wall of the groove 64 forms the collection well 54 when the separation vessel 52 expands in response to fluid and particles in the separation vessel 52 or in response to centrifugal forces. As shown in FIG. 2, the top surface of the rotor 12 preferably includes retainer grooves for receiving the first and second lines 28 and 30, three-way connector 34, line 48, particle concentrate line 58, and fluid outlet line 62.

The fluid outlet line 62 is fluidly coupled to a fluid collection container 66 for optionally collecting part of the fluid removed from the separation vessel 52, and the particle concentrate line 58 is fluidly coupled to one or more particle collection containers 70 for collecting particles removed from the separation vessel 52. Preferably, the particle concentrate line 58 includes a pump loop or outlet pump loop 72 capable of being mounted in a peristaltic pump for pumping particles through the particle concentrate line 58. The pump for pump loop 72 regulates the flow rate and concentration of particles in particle concentrate line 58. The white blood cells of interest or desired particles will be collected into one of the containers 70. It is understood that any number of containers 70 can be used to collect the desired subsets of white blood cells.

FIG. 1 illustrates three collection bags for the blood cells of interest. Platelets can also be collected in a separate bag if desired. After sedimentation in chamber 18 red blood cells can be removed through inlet 22 to inlet line 32. The red blood cells then pass through Y connector 34 to line 30. Line 30 is fluidly coupled to a red blood cell collection container or cell collection container 31 for collecting red blood cells collected during the procedure. Preferably the red blood cell collection line or conduit 30 includes a pump loop 46 capable of being mounted in a peristaltic pump for controlling the flow of red blood cells through line 30 and out through inlet 22.

To control the flow rates of the various substances and cells and the rotational speed of the rotor 12 during operation of the system 10, a controller is provided. The controller (not shown) controls pumps (not shown) for pumping substances through the pump loops 43, 44, 46 and 72 and controls a motor (not shown) for rotating the centrifuge rotor 12.

Fluid and particles from the first source 38 are connectable by line 17 and pump loop 43 associated with a peristaltic pump to air chamber 47. Also, diluting, sedimentation, or elutriation fluids from source 42 are connectable by line 37 and pump loop 44 associated with a peristaltic pump to air chamber 47. Air chamber 47 provides an inlet filter for filtering aggregates prior to particle separation. The air chamber 47 acts as a bubble trap and an air detection chamber. The air chamber 47 further functions as a fluid pulse suppressor. Use of air chamber 47 is optional, however, and it is also understood that it can be omitted from the source delivery configuration.

A recirculation line or conduit 67 is connected from line or conduit 62 to fluid inlet line or conduit 37. A slide clamp or other flow controlling element 49 is on line 37 and a slide clamp or other flow controlling element 68 is on line 62. Substantially cell-free and plasma-free media or fluid can be directed through line 67 to upstream of inlet pump loop 44. This allows diluting buffer or media to be re-circulated. The initial media or fluid from the separation vessel 52 may contain plasma or cells undesirable for recirculation. This initial media or fluid is directed to fluid collection container 66 prior to initiation of the recirculation process. Although the invention is described in connection with a blood component separation process and specifically a white blood cell separation or fractionation process, it should be understood that the invention in its broadest sense is not so limited. The invention may be used to separate a number of different types of particles.

Initially, blood is collected from a patient and this blood is separated in a centrifugal separation process to isolate what is known as a blood product containing white blood cells. During this initial centrifugation process, platelet rich plasma and a portion of the red blood cells and more dense white blood cells may be separated from the blood, leaving the resulting white blood cell product. In addition, this resulting blood product most likely includes some platelets and red blood cells. Not all starting blood products will require an initial centrifugal separation. For example, collected blood from umbilical cords is generally not subject to an initial centrifugal separation. The starting blood product will then be provided from first source 38.

The initial separation of the collected blood is preferably performed on a centrifuge (not shown) separate from the system 10, such as a dual stage or single stage centrifugal separator. In an alternative embodiment, the centrifuge rotor 12 may include structure for providing initial blood component separation on the centrifuge rotor 12, as disclosed in above-referenced U.S. Pat. No. 5,674,173. The separated blood product could also be collected and initially separated by other methods.

The resulting separated or collected blood product is placed in the first source 38 although the blood product could also come directly from a separation system through a line (not shown). The first source 38 is coupled to the first line 28 through line 17. In addition, the second source 42 containing the diluting, sedimentation or elutriation fluid is coupled to the line 28 through the line 37. The centrifuge rotor 12 is rotated about the axis of rotation A—A, at approximately 2400 rpm, although other speeds can be used. The blood product is pumped from source 38 through pump loop 43 and loaded into the fluid chamber 18 at a flow rate selected to give the desired packing of the loaded product for the selected centrifuge speed. The pump associated with loop 43 is stopped to stop flow of blood product from source 38. Flow of diluting, sedimentation or elutriation fluid is then started using pump loop 44 and the action of its associated pump to rinse line 28 and/or wash the loaded blood product. The diluting, sedimentation fluid or elutriation fluid passes through line 28 and Y connector 34, and inlet line 32 into the inlet 22 of chamber 18.

The inlet pump associated with the pump loop 44 is stopped to stop the flow of low density diluting sedimentation or elutriation fluid into the chamber 18. As the centrifuge continues to rotate, the particle constituents loaded in the chamber separate by sedimentation under the resulting centrifugal force. After sedimentation of the particle constituents of the blood product, the pump associated with pump loop 46 is activated to remove at a low flow rate the sedimented red blood cells through the inlet 22 of the chamber 18 and then through inlet line 32 and line 30 to container 31 if reduction of red blood cells is required. After the reduction of fractionated red blood cells, the white blood cells remaining in chamber 18 can be further separated by elutriation or the inlet pump associated with pump loop 43 can be restarted to reintroduce a second batch of blood product from source 38 into chamber 18.

The elutriating step for separating white blood cells into the desired subsets can be done after each procedure or after the source 38 is empty of blood product. The only requirement is that there be a sufficient number of white blood cells in chamber 18 to achieve effective separation or fractionation. Therefore, the white blood cell content of the starting blood product should be considered in determining the sequence order of the elutriation step.

For collection of fractionated or separated white blood cells or other separated particles, an operator, after the first source 38 is empty, slowly increases the inlet pump speed associated with pump loop 44, decreases the centrifuge speed, or increases the density or viscosity of the diluting, sedimentation or elutriation fluid to separate the cells in chamber 18 into subsets by elutriation, as is well known in the art. The elutriation, sedimentation or diluting fluid used for separation initially flows into fluid collection container 66 as the initial flows of such fluid may contain plasma or starting cell suspension media. After clamp 68 is closed the more cell-free and substantially plasma free fluid flows through the recirculation line or line 67, wherein it is pumped by loop 44 for re-use through optional air chamber 47, line 28, connector 34, and inlet line 32 to the inlet 22 of chamber 18. The process then continues until the desired separation of cells in chamber 18 and the desired volume reduction of cells using the separation vessel 52 is achieved.

The controller maintains the rotation speed of the rotor 12 within a predetermined rotational speed range to facilitate formation of a fluidized bed. In addition, the controller regulates the pumps to convey fluid at a predetermined flow rate through the inlet line 32 and into the inlet 22 of the fluid chamber 18. These flowing blood components displace priming fluid from the fluid chamber 18. When the platelet and white blood cell particles enter the fluid chamber 18, they are subjected to two opposing forces. Fluid flowing through the fluid chamber 18 with the aid of a pump establishes a first viscous drag force which urges the particles toward the outlet 20. A second centrifugal force created by rotation of the rotor 12 and fluid chamber 18 acts to urge the particles toward the inlet 22.

In another, non-elutriation application, the controller may regulate the rotational speed of the rotor 12 and the flow rate of the pump to collect platelets and white blood cells in the fluid chamber 18. As plasma flows through the fluid chamber 18, the flow velocity of the plasma decreases and reaches a minimum as the plasma flow approaches the maximum cross-sectional area of the fluid chamber 18. Because the rotating centrifuge rotor 12 creates a sufficient gravitational field in the fluid chamber 18, the platelets accumulate near the maximum cross-sectional area of the chamber 18, rather than flowing from the chamber 18 with the plasma. The white blood cells accumulate somewhat radially outward from the maximum cross-sectional area of the chamber 18. However, density inversion tends to mix these particles slightly during this initial establishment of the fluidized particle bed.

The fluid chamber 18, as shown in FIGS. 3, 4, 5, and 6, is configured to allow cyclic collection of selected particles, such as white blood cells, followed by efficient evacuation of the cells into a collection bag 70. In contrast to other chamber designs for forming fluidized beds, the fluid chamber described herein has particular application for the automated collection of blood components in that a bolus of cells having selected characteristics can be collected in the fluid chamber 18 and then flushed with low density fluid into a collection bag and these steps can be repeated multiple times, allowing a larger quantity of the selected cells to be collected from the donor or patient while reducing the amount of time necessary for the donation process. When a quantity of cells have been collected in the fluid chamber 18, the flow of fluid through the chamber can be increased and the collected cells can be washed out of the chamber and directed into a collection bag.

The fluid chamber 18 comprises a flared entry section 176, a main or transition section 180, and a separating section 182 (FIG. 6). The entry section 176 has a shape that minimizes the rate of fractional change in velocity, momentum or kinetic energy per unit distance along the flow axis. That is, the normalized deceleration from the inlet 22 to the main or transition section 180 is minimized by virtue of being constant. The objective is to minimize the tendency for laminar mixing in the fluid where the change in fluid velocity is greatest, that is, in the entry section. The separation section 182 is shaped such that the critical angle of the particle escape condition occurs at the maximum chamber area, and this critical angle is approached slowly. The critical angle escape condition occurs when the fractional decrease in velocity per unit distance in the direction of flow is equal to the fractional decrease in the centrifugal field with unit distance. The normalized deceleration should be minimized from the end of the main or transition section to the end of the separation section. The objective is to maximize the sensitivity of the particle escape conditions to sedimentation velocity, increasing discrimination between cell types based on flow conditions.

The fluid chamber 18 may be constructed in two pieces, a main body 166 and a cap 168. In a preferred embodiment, both pieces may be symmetrical around an axis 170 or axis of symmetry. The main body 166 has an inlet 22 comprising a through bore 172 and a concentric stopped bore 174. The diameter of the through bore 172 corresponds to the inside diameter of the first inlet line 32, while the diameter of the stopped bore 174 corresponds to the outside diameter of the first inlet line 32, so that the inlet line 32 can be seated in the stopped bore 174 and a fluid passageway of constant diameter can be formed between the inlet line 32 and the through bore 172. The through bore 172 opens into a flared section 176 or entry section. A wall 178 of the flared section 176 tapers away from the axis 170. The outwardly flared curve of the cell entry chamber is generally defined by $$A = (A_0)\exp(CeXe)$$

where

A is the area perpendicular to the axis of symmetry at Xe;

$A_0$ is the area perpendicular to the axis of symmetry at the inlet;

Xe is the distance along the axis of symmetry from the inlet, 0<Xe<Le;

Le is the length of the entry section; and

Ce is a design constant for the entry section, determined by design constraints.

$$Ve = (A - A_0)/Ce$$

where

Ve is the volume between $A_0$ and A.

The wall of the entry section, comprising an outwardly flared curve forming a first surface, preferably a surface of rotation, about the axis of symmetry, has an axial length Xe and an inmost maximum diameter Ae perpendicular to the axial length. The axial length Xe may be greater than the inmost maximum diameter Ae.

Immediately adjacent to and down stream from the flared section 176, a main or transition section 180 extends from the flared section 176 to a separation section 182 of the main body 166. A wall 184 of the main section 180 transitions smoothly between the wall 178 of the flared section 176 and a wall 186 of the separation section 182.

The wall 186 of the separation section comprises a first inward curve forming a second surface, preferably a surface of rotation, about the axis of symmetry 170. The first inward curve is generally defined by $$A = A\text{smax} - (A\text{smax} - Am)\exp(-CsXs)$$

where

A is the area perpendicular to the axis of symmetry at Xs;

Asmax is the asymptotic area of the separation section;

Am is the maximum actual area of the main section;

Xs is the distance along the axis of symmetry from the beginning of the separation section, 0<Xs<Ls;

Ls is the length of the separation section; and

Cs is a design constant for the separation section, determined by design constraints.

$$Vs = A\text{smax}Xs - (A - Am)/Cs$$

where

Vs is the volume for the separation section between Am and A.

The transition or main section between the entry section and the separation section has a wall 184 comprising a second inward curve forming a third surface, preferably a surface of rotation, about said axis of symmetry, said second inward curve being different from said first inward curve. The first curve may be tangent to the second curve at a first junction between the first and second curves and the second curve may be tangent to the third curve at a second junction between the second and third curves. The main section has a shape defined by $$A = A\text{mmax} - (A\text{mmax} - Ae)\exp(-CmXm)$$

where

A is the area perpendicular to the axis of symmetry at Xm;

Ammax is the asymptotic area of the main section,

Xm is the distance along the axis of symmetry from the end of the entry section (also, the beginning of the main section), $0 < Xm < Lm$, Lm is the length of the main section, and Cm is a design constant for the separation section, determined by design constraints.

$$Vm = Ammax Xm - (A - Ae)/Cm$$

where

Vm is the volume for the main section between A and Am.

As blood components such as plasma, platelets and white blood cells flow into the fluid chamber 18, they are affected by rotational speed, coriolis forces, fluid flow rate, and the configuration of the fluid chamber. For example, in the entry section, fluid flow rate will decrease as the cross sectional area of the section increases. At the same time, the blood components are subject to a centrifugal force resulting from the rotation of the apparatus. The centrifugal force experienced by a particle in the section will decrease as the particle moves radially inward toward the axis of rotation. The sizes of white blood cells are distributed about an average sedimentation velocity.

The determination of the design constants Cs, Ce and Cm may be developed in the following manner. Initially, the designer specifies the maximum chamber capacity for each type of cell to be accommodated simultaneously, based on a selected fluid flow rate and centrifugal speed. The design is constrained by the rotor geometry and available space. Empirical information may relate cell capacity to the flow rate, centrifugal speed and available space. Usually this will be a maximum permissible chamber volume. An iterative process utilizing a computerized model, for example, a spread sheet incorporating the relationships described above, may be employed to adjust the shape constants Cs, Ce, Cm, Ammax and Asmax in conjunction with the lengths Le, Lm and Ls.

In previous designs for cell separation chambers, it has been observed that incoming cells tend to flow along one side of the chamber due to coriolis forces until the conditions of a fluidized bed are established in the chamber. In the present design, the cell level appears to rise evenly without mixing, as the velocity of the particles tends to be substantially constant across the outwardly flared entry section 176. The main or transition section 180 allows for a smooth transition, and provides cell storage capacity, while the separation section 182 allows the collected bolus of cells to be expressed out of the cell separation chamber as described herein. It is believed that the chamber shape described herein provides relatively constant fractional changes in momentum of particles within the entry and separation sections, increasing the effectiveness and efficiency of cell collection.

The selected particles begin to enter the fluid chamber 18. Because of the flared shape of the entry section 176, the flow velocity across the main section 180 becomes more uniform across the entire cross-section of the chamber 18. A relatively flat velocity distribution makes it more likely that the desired cells will be captured in the separation section 182. Captured white blood cells begin to form a bolus. When the separation section 182 is sufficiently filled with the desired particle, such as white blood cells, the fluid chamber 18 can be purged. After purging, the flow rate through the chamber 18 can be increased to flush or evacuate the accumulated particles into the separation vessel 52. Because a cycle of collecting cells in the fluid chamber and evacuating the collected cells to the collection bag can be performed multiple times, a relatively large amount of a rarer blood component, such as white blood cells, can be collected from a single donor or patient.

Figure 7:
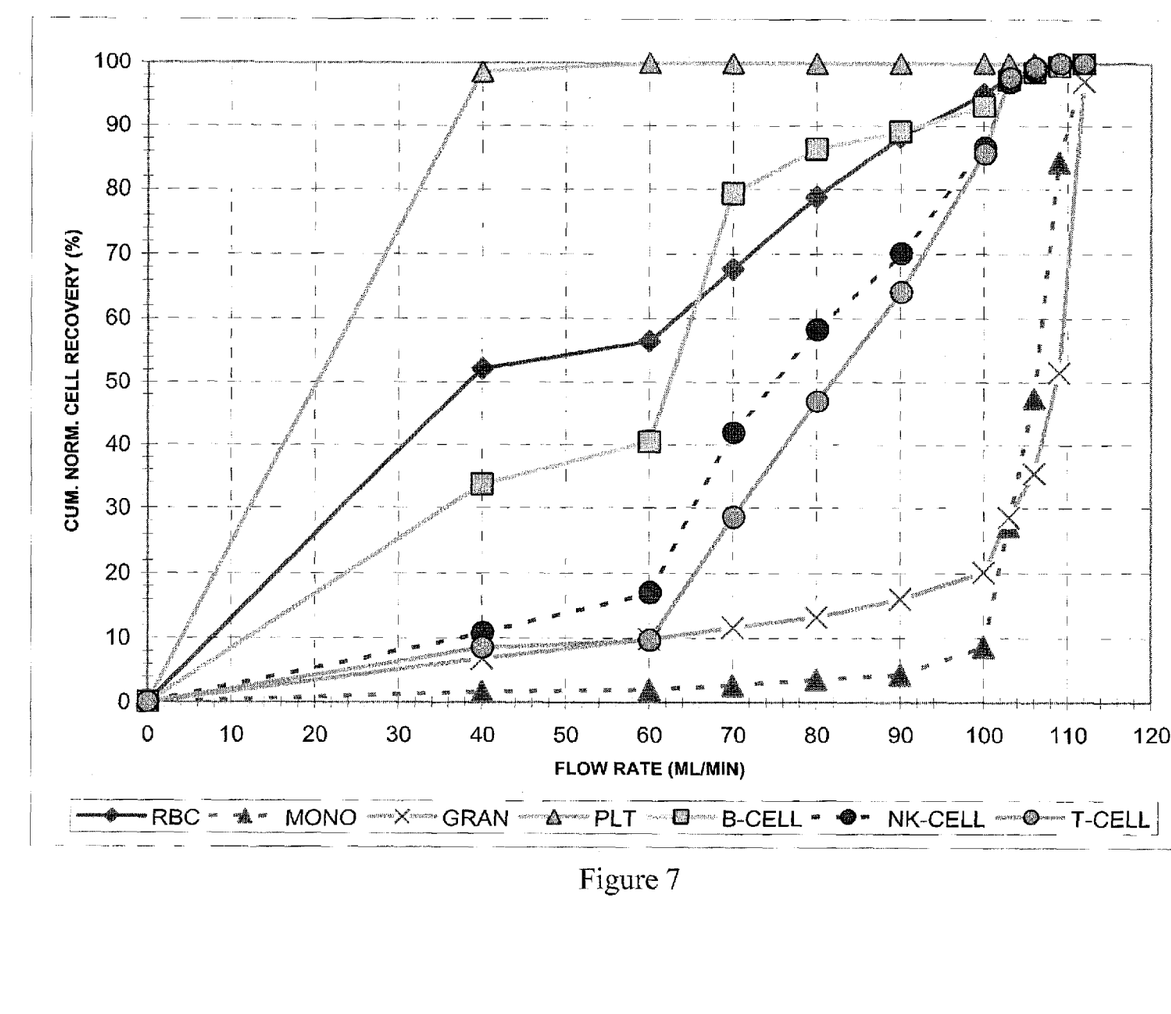
FIG. 7 is a graph of cell separation data for the fluid separation chamber described herein.
Figure 8:
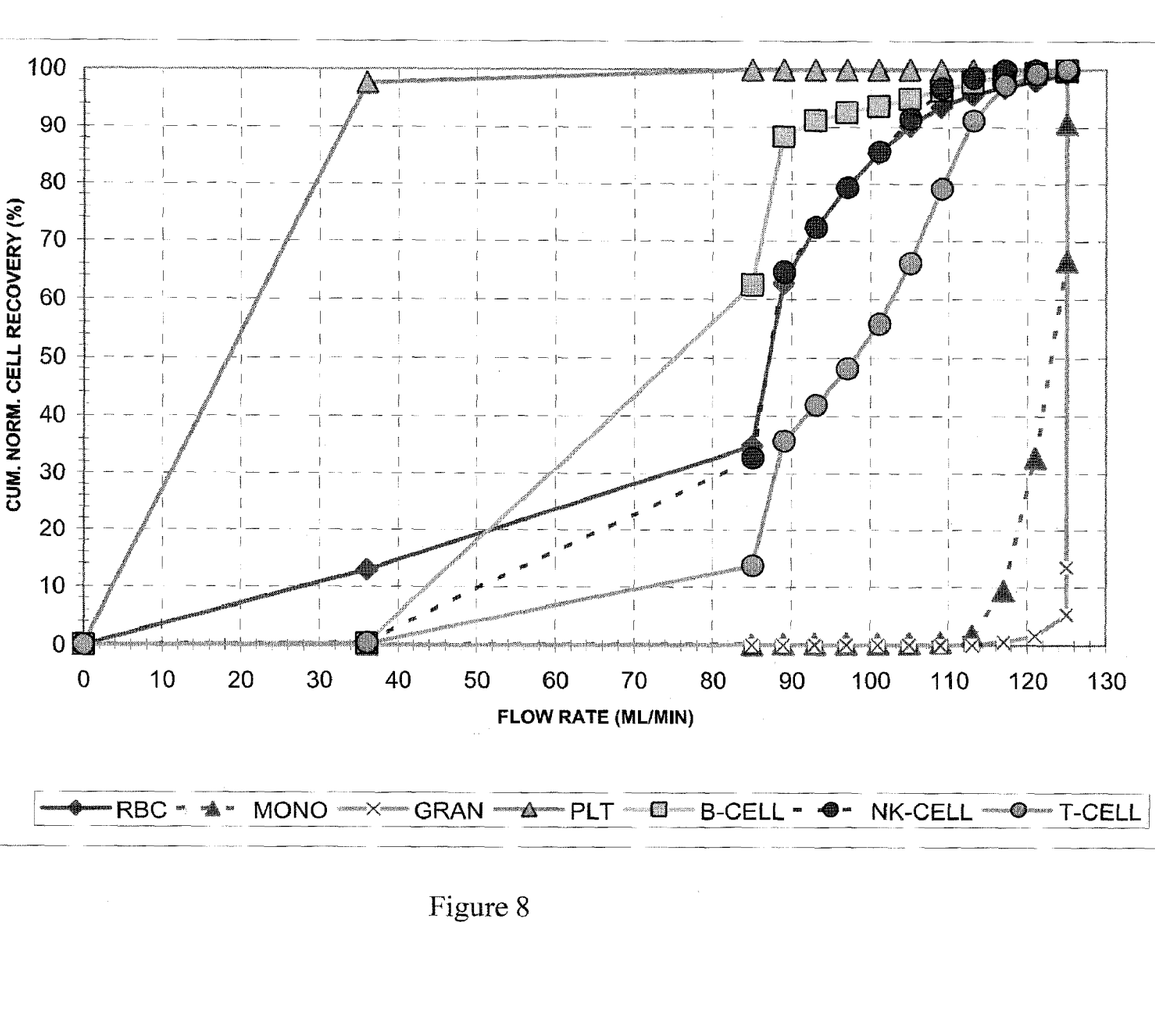
FIG. 8 is a graph of cell separation data for a smooth cone separation chamber.

FIG. 7 illustrates an experimental performance of a chamber in accordance with the present invention compared to a smooth cone elutriation chamber available from the assignee of this invention, the performance of which is shown in FIG. 8. The graphs illustrate the separation of different blood components, including platelets, red blood cells, monocytes, granulocytes, and lymphocytes such as B-cells, NK cells, and T cells. The graph of FIG. 7 illustrates that, as flow increases, certain cell types such as red blood cells, B-cells, NK-cells and T-cells are expressed out of the chamber at more distinct flow rates as compared to the performance of the smooth cone chamber illustrated in FIG. 8. In FIG. 8, all four of the certain cell types express out of the chamber at flow rates between 80 and 90 mL/min. In FIG. 7, these cell types express out of the chamber described herein at flow rates between 40 and 90 mL/min. This larger range would allow for more selective separation of cell types.

In the illustrated embodiment, the main body 166 of the fluid chamber 18 further comprises a circumferential flange 188, which is supported in the holder 16. The size of the flange may be varied so that different types of fluid chambers can be used in a single centrifuge apparatus. Since certain chambers available from Gambro BCT, Inc. are relatively larger in diameter than the fluid chamber described herein, the flange may be designed to compensate for these differences. A plurality of radial fins 189 is formed proximally from the flange 188. In this embodiment, the fins serve primarily for stability when the fluid chamber 18 is mounted in an existing holder and also as lines for plastic material during injection molding of the main body 166. At the distal end of the main body 166, a groove 190 secures the cap 168 to the distal end. The cap comprises a rim 191 that fits into the groove 190 and a flange 192 which fits against the distal end of the main body. The cap and main body may be joined by ultrasonic welding, or other suitable technique as known in the art. The cap opens into an abrupt frustro-conical section 194. The abrupt section 194 tapers towards the axis 170, the inner wall 196 of the abrupt section 194 forming a 120° included angle. The included angle is not critical, but it is preferred that the frustro-conical section 194 be relatively short. The abrupt furstro-conical section 194 funnels collected blood components flushed from the main section 180 and the separation section 182 into the outlet 20 without excessive turbulence or damage to the blood components. The outlet 20 comprises a through bore 198 and a concentric stopped bore 200. The diameter of the through bore 198 corresponds to the inside diameter of the outflow tubing 30, while the diameter of the stopped bore 200 corresponds to the outside diameter of the outflow tubing 30, so that the outflow tubing 30 can be seated in the stopped bore 200 and a fluid passageway of constant diameter can be formed between the outflow tubing 30 and the through bore 198. The through bore 198 opens into the frustro-conical section 194.

Although the inventive device and method have been described in terns of removing white blood cells and collecting platelets, this description is not to be construed as a limitation on the scope of the invention. The invention may be used to separate any of the particle components of blood from one another or the invention could be used in fields other than blood separation. For example, the fluidized bed may be formed from red blood cells to prevent flow of white blood cells through the fluid chamber 18, so long as the red blood cells do not clump excessively. Alternatively, the liquid for carrying the particles may be saline or another substitute for plasma. In addition, the invention may be practiced to remove white blood cells or other components from a bone marrow harvest collection or an umbilical cord cell collection harvested following birth. In another aspect, the invention can be practiced to T cells, stem cells, or tumor cells. Further, one could practice the invention by filtering or separating particles from fluids unrelated to either blood or biologically related substances. Applications using the Trima® apheresis machine may include using a fluidized bed to separate white blood cells and remaining red blood cells from platelets by continuous rather than batch processing. And to collect the separated platelets.

It will be apparent to those skilled in the art that various modifications and variations can be made to the structure and methodology of the present invention without departing from the scope or spirit of the invention. Rather, the invention is intended to cover modifications and variations provided they come within the scope of the following claims and their equivalents.

What is claimed is:

1. A cell separation chamber configured to be mounted on a rotor, said rotor having an axis of rotation, said cell separation chamber having an axis of symmetry and comprising
   an inlet for biologic fluids on said axis mountable radially outwardly from said axis of rotation, said inlet having a coupling for an inlet line, and
   an outlet on said axis of symmetry mountable radially inwardly from said inlet towards said axis of rotation, said outlet comprising a cap having a frustro-conical section tapering towards said axis and a coupling for an outlet line at an apex of said frustro-conical section,
   an entry section extending radially inwardly from said inlet, said entry section having a wall comprising an outwardly flared curve forming a first surface of rotation about said axis, said entry section having an axial length along said axis of said cell separation chamber and an inmost maximum diameter perpendicular to said axial length, and at least one section spaced radially inwardly from said entry section, said at least one section having a wall comprising an inward curve forming a surface of rotation about said axis.

2. The cell separation chamber according to claim 1 wherein said axial length is greater than said inmost maximum diameter.

3. The cell separation chamber according to claim 1 wherein said outwardly flared curve is generally defined by $$A=(A_0)\exp(CeXe)$$

where
   A is the area at Xe;
   $A_0$ is the area at the inlet;
   Xe is the distance along the axis from the inlet, 0<Xe<Le;
   Le is the length of the entry section, and
   Ce is a constant defined by $Ve=(A-A_0)/Ce$ where Ve is the volume between $A_0$ and A.

4. The cell separation chamber according to claim 1 further comprising a separation section spaced downstream from said entry section, said separation section having a wall comprising a first inward curve forming a second surface of rotation about said axis.

5. The cell separation chamber according to claim 4 wherein said first inward curve is generally defined by $$A=Asmax-(Asmax-Am)\exp(-CsXs)$$

where
   A is the area perpendicular to the axis of at Xs;
   Asmax is the asymptotic area of the separation section;
   Am is the maximum actual area of the main section;
   Xs is the distance along the axis from the beginning of the separation section, 0 <Xs <Ls;
   Ls is the length of the separation section; and
   Cs is a constant defined by $Vs=AsmaxXs-(A-Am)/Cs$ where Vs is the volume for the separation section between Am and A.

6. The cell separation chamber according to claim 4 further comprising a transition section between said entry section and said separation section, said transition section having a wall comprising a second inward curve forming a third surface of rotation about said axis, said second inward curve being different from said first inward curve.

7. The cell separation chamber according to claim 6 wherein said first curve is tangent to said second curve at a first junction between said first and second curves.

8. The cell separation chamber according to claim 7 wherein said second curve is tangent to said outwardly flared curve at a second junction between said second curve and said outwardly flared curve.

9. The cell separation chamber according to claim 8 wherein said second inward curve is generally defined by $$A=Ammax-(Ammax-Ae)\exp(-CmXm)$$

where
   A is the area perpendicular to the axis at Xm;
   Ammax is the asymptotic area of the transition section,
   Xm is the distance along the axis from the end of the entry section, 0 <Xm <Lm,
   Lm is the length of the transition section, and
   Cm is a constant defined by $Vm=AmmaxXm-(A-Ae)/Cm$ where Vm is the volume for the main section between A and Am.

10. The cell separation chamber according to claim 9 wherein said first inward curve is generally defined by $$A=Asmax-(Asmax-Am)\exp(-CsXs)$$

where
   A is the area perpendicular to the axis of at Xs;
   Asmax is the asymptotic area of the separation section;
   Am is the maximum actual area of the main section;
   Xs is the distance along the axis from the beginning of the separation section, 0<Xs<Ls;
   Ls is the length of the separation section; and
   Cs is a constant defined by $Vs=AsmaxXs-(A-Am)/Cs$ where Vs is the volume for the separation section between Am and A.

11. A disposable cell separation set configured to be mounted on a centrifugal cell separation apparatus, said apparatus having rotor with an axis of rotation, said disposable cell separation set comprising
   access means for connecting said cell separation set to a source of cell-containing fluid;
   a separation vessel;
   at least one bag for receiving separated cells,
   at least one means for engaging a pump to force fluid through said cell separation set;
   a cell separation chamber in fluid communication with said separation vessel and having an axis and an inlet and an outlet on said axis, said cell separation chamber having an entry section extending radially inwardly from said inlet, said entry section having a wall comprising an outwardly flared curve forming a first surface of rotation about said axis, said entry section having an axial length and an inmost maximum diameter perpendicular to said axial length, and at least one section spaced radially inwardly from said entry section, said at least one section having a wall comprising an inward curve forming a surface of rotation about said axis; and a plurality of conduits connecting at least some of said access means, said separation vessel, said pump-engaging means, said bag, and said cell separation chamber.

12. The cell separation set according to claim 11 wherein said axial length is greater than said inmost maximum diameter.

13. The cell separation set according to claim 11 wherein said outwardly flared curve is generally defined by $$A=(A_0)\exp(CeXe)$$

where

A is the area at Xe;

$A_0$ is the area at the inlet;

Xe is the distance along the axis from the inlet, $0<Xe<Le$;

Le is the length of the entry section; and

Ce is a constant defined by $Ve=(A-A_0)/Ce$ where Ve is the volume between $A_0$ and A.

14. The cell separation set according to claim 11 wherein said at least one section further comprises a separation section spaced downstream from said entry section, said separation section having a wall comprising a first inward curve forming a second surface of rotation about said axis.

15. The cell separation set according to claim 14 wherein said first inward curve is generally defined by $$A=Asmax-(Asmax-Am)\exp(-CsXs)$$

where

A is the area perpendicular to the axis of at Xs;

Asmax is the asymptotic area of the separation section;

Am is the maximum actual area of the main section;

Xs is the distance along the axis from the beginning of the separation section, $0<Xs<Ls$;

Ls is the length of the separation section; and

Cs is a constant defined by $Vs=AsmaxXs-(A-Am)/Cs$ where Vs is the volume for the separation section between Am and A.

16. The cell separation set according to claim 14 wherein said at least one section further comprises a transition section between said entry section and said separation section, said transition section having a wall comprising a second inward curve forming a third surface of rotation about said axis, said second inward curve being different from said first inward curve.

17. The cell separation set according to claim 16 wherein said first curve is tangent to said second curve at a first junction between said first and second curves.

18. The cell separation set according to claim 17 wherein said second curve is tangent to said third curve at a second junction between said second and third curves.

19. The cell separation set according to claim 18 wherein said second inward curve is generally defined by $$A=Ammax-(Ammax-Ae)\exp(-CmXm)$$

where Ammax is the asymptotic area of the transition section,

Xm is the distance along the axis of symmetry from the end of the entry section, $0<Xm<Lm$, Lm is the length of the transition section, and Cm is a constant defined by $Vm=AmmaxXm-(A-Ae)/Cm$ where Vm is the volume for the main section between A and Am.

20. The cell separation set according to claim 19 wherein said first inward curve is generally defined by $$A=Asmax-(Asmax-Am)\exp(-CsXs)$$

where

A is the area perpendicular to the axis of at Xs;

Asmax is the asymptotic area of the separation section;

Am is the maximum actual area of the main section;

Xs is the distance along the axis from the beginning of the separation section, $0<Xs<Ls$;

Ls is the length of the separation section; and

Cs is a constant defined by $Vs=AsmaxXs-(A-Am)/Cs$ where Vs is the volume for the separation section between Am and A.

* * * * *